US012672954B2

(12) United States Patent
Ghorbani

(10) Patent No.: US 12,672,954 B2
(45) Date of Patent: Jul. 7, 2026

(54) BREAST IMPLANT ENHANCEMENT DEVICE

(71) Applicant: Nourollah Ghorbani, Walnut Creek, CA (US)

(72) Inventor: Nourollah Ghorbani, Walnut Creek, CA (US)

(*) Notice: Subject to any disclaimer, the term of this patent is extended or adjusted under 35 U.S.C. 154(b) by 0 days.

(21) Appl. No.: 18/462,303

(22) Filed: Sep. 6, 2023

(65) Prior Publication Data

US 2024/0074845 A1 Mar. 7, 2024

Related U.S. Application Data

(60) Provisional application No. 63/404,029, filed on Sep. 6, 2022.

(51) Int. Cl.
*A61F 2/12* (2006.01)

(52) U.S. Cl.
CPC ...................................... *A61F 2/12* (2013.01)

(58) Field of Classification Search
CPC ...... A61F 2230/0063; A61F 2230/0067; A61F 2230/0071; A61F 2250/006; A61F 2250/0063; A61F 2250/0062; A61F 2/12
See application file for complete search history.

(56) References Cited

U.S. PATENT DOCUMENTS

2015/0351900 A1* 12/2015 Glicksman ............. A61B 90/94
623/8
2020/0008929 A1* 1/2020 Bertoli ...................... A61F 2/12
2023/0233737 A1* 7/2023 Contiliano .............. A61L 27/52
424/423

* cited by examiner

*Primary Examiner* — William H Matthews
(74) *Attorney, Agent, or Firm* — West & Associates, A PC; Stuart J. West; Charlotte Rodeen-Dickert

(57) ABSTRACT

A breast implant enhancement device can be placed behind a breast implant (between the implant and the chest wall) to reduce or eliminate appearance of wrinkles or folds on the outer surface of the implant against the skin. A breast implant enhancement system comprising an enhancement element adapted and configured to be selectively coupled with the posterior surface of a breast implant, wherein said enhancement element has at least one angular edge.

13 Claims, 8 Drawing Sheets

PRIOR ART

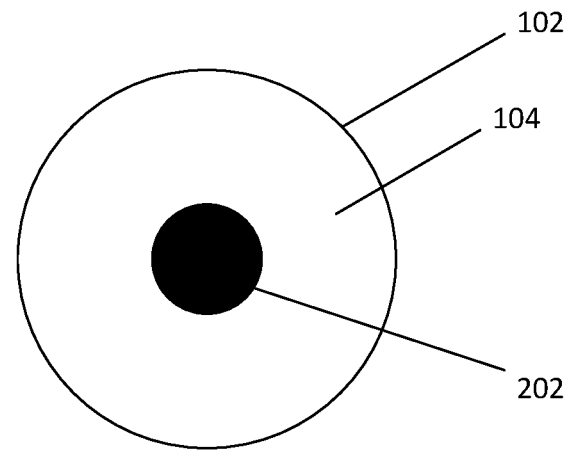
Fig. 2a
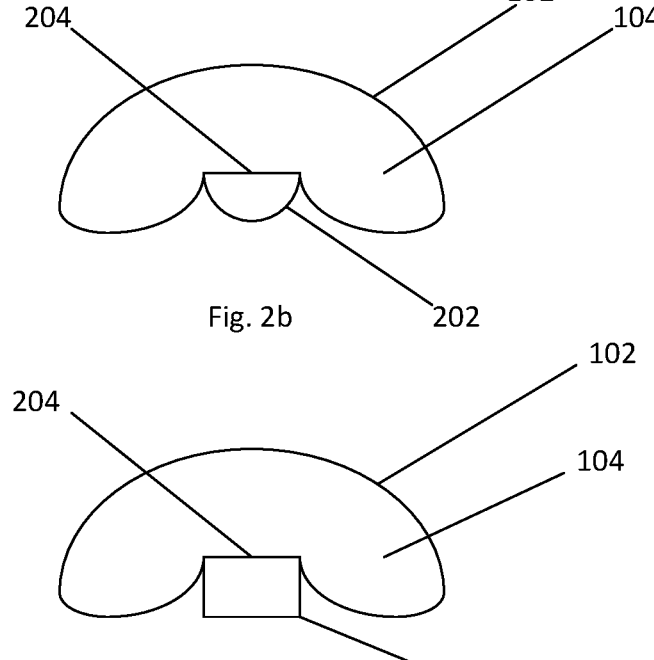
Fig. 2b
Fig. 2c
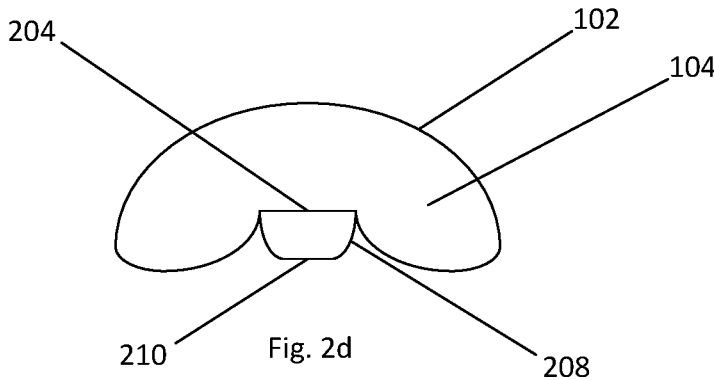
Fig. 2d

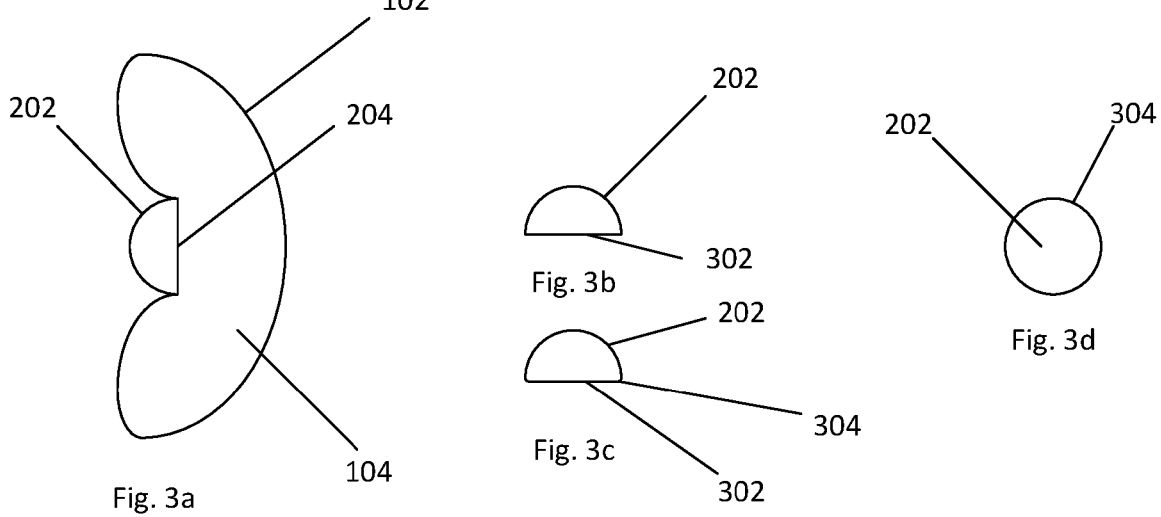
Fig. 3a
Fig. 3b
Fig. 3c
Fig. 3d
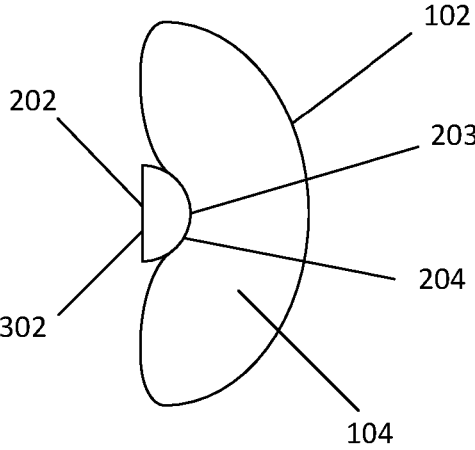
Fig. 3e

BREAST IMPLANT ENHANCEMENT DEVICE

CROSS-REFERENCE TO RELATED APPLICATION(S)

This application claims the benefit of priority of U.S. Provisional Patent Application 63/404,029 filed Sep. 6, 2022, by Nourollah Ghorbani, the complete contents of which are hereby incorporated herein by reference.

BACKGROUND

Technical Field

The present device relates to the field of cosmetic and plastic surgery and more specifically to the field of breast implant technology.

Background

Breast implants are often used in breast enhancement and reconstructive procedures. Commonly breast implants 100 comprise a volume of silicone gel or saline 104 contained within a flexible membrane 102 usually comprised of silicone rubber or polysiloxane(s) material. The flexible membrane 102 is typically pre-filled with a known volume of silicone gel 104 via an aperture on the inward facing side of the implant which is later sealed via a cover comprised of the same silicone rubber or polysiloxane(s) material. Due to the method of implant and depending on various factors such as skin thickness, occasionally folding or rippling 106 in the breast implant's outer flexible membrane (See FIGS. 1*a*-1*c*) may be evident through or on the skin's surface. Such is partially due to gravity and the way the implant is suspended. What is needed is an apparatus adapted and configured to eliminate such visible folding and/or rippling.

BRIEF DESCRIPTION OF THE DRAWINGS

Further details of the present device are explained with the help of the attached drawings in which:

FIGS. 2*a*-2*d* depict embodiments of a device for reducing or eliminating folding and/or rippling of an implanted breast implant.

FIGS. 3*a*-5*e* depict alternate embodiments of a device for reducing or eliminating folding and/or rippling of an implanted breast implant.

DETAILED DESCRIPTION

Figures 1A, 1B, 1C:
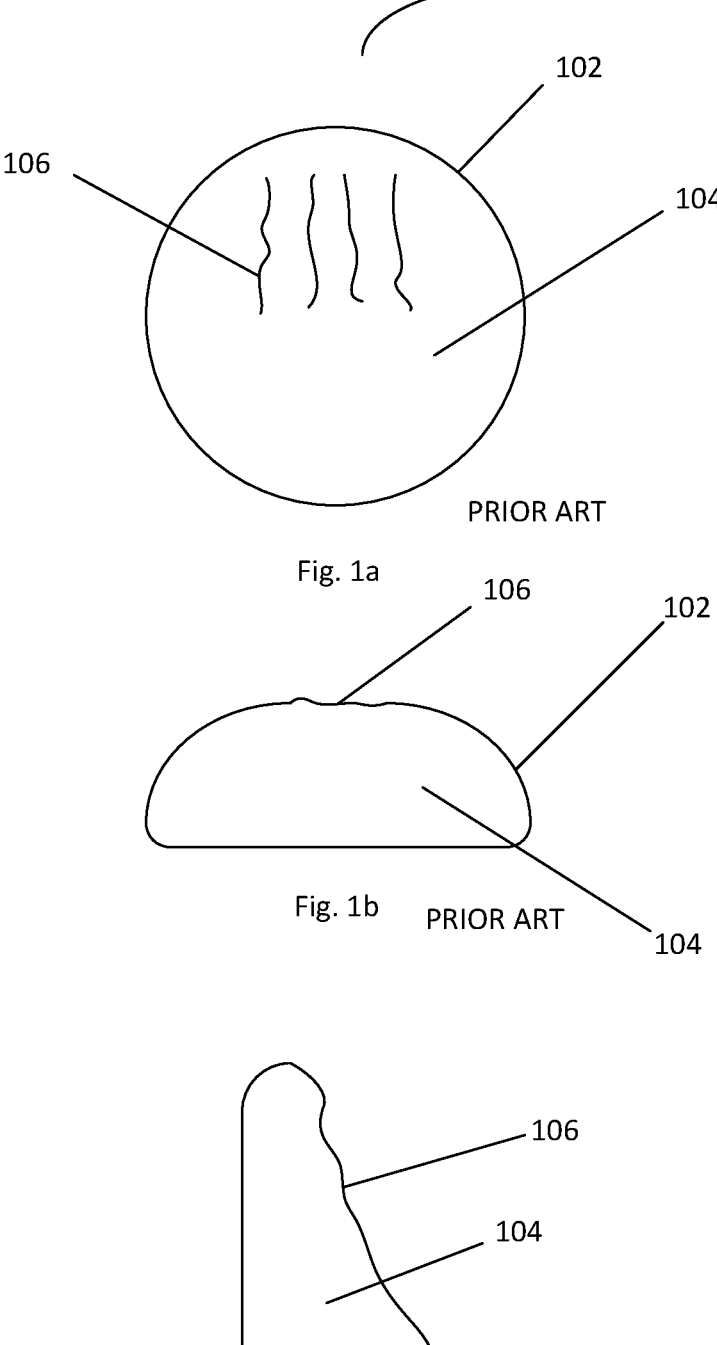
FIGS. 1*a*-1*c* depict a prior art example of a breast implant exhibiting folding and/or rippling.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

FIGS. 2*a*-*d* depict embodiments of a system for reducing or eliminating folding 106 and/or rippling of an implanted breast implant 100. In the embodiment depicted in FIGS. 2*a*-2*d*, an enhancement element 202 can be coupled with the inward facing side of the flexible membrane 102 of a breast implant 100. In some embodiments, the enhancement element can be comprised of a solid material adapted and configured for placement within the body and in some embodiments can be comprised of solid silicone. However, in alternate embodiments the enhancement element 202 can be a hollow bodied element and/or comprised of a substantially rigid outer shell filled with a differing substance, such as, but not limited to silicone gel and/or saline. While in some embodiments the enhancement element 202 can be comprised of solid silicone, in alternate embodiments the enhancement element 202 can be comprised of any known, convenient and/or desired material and/or materials adapted and/or configured to be placed within the human body.

In some embodiments, the enhancement element 202 can be coupled with the posterior side of the flexible membrane 102 of an implant 100 via a friction weld and/or an adhesive at an attachment region. However, in alternate embodiments, the enhancement element 202 can be removably and/or fixedly coupled with the posterior side of the flexible membrane 102 of an implant 100 in any known, convenient and/or desired manner using any known, convenient and/or desired attachment mechanism. In some embodiments an attachment region 204 can be proximate to the covered aperture on the inward facing (posterior) side of the breast implant 100. However, in alternate embodiments, an attachment region 204 can be located in any known, convenient and/or desired location on the inward facing side of a breast implant 100.

In some embodiments an enhancement element 202 can be substantially dome-shaped 203 with a substantially flat backside 205, as shown in FIG. 2*b*. However, in alternate embodiments an enhancement element 202 can have a substantially tubular shape 206, as shown in FIG. 2*c*, and/or truncated substantially dome shape 208 with at least two substantially flat surfaces 210 of a greater and smaller area, as shown in FIG. 2*d*. In still further embodiments, an enhancement element 202 can have any known, convenient and/or desired shape.

As shown in FIG. 2*b*, an enhancement element 202 having a dome shape 203 can be oriented such that the dome portion 203 can be pointing outward from the posterior surface of an implant 102. As shown in FIG. 2*d*, an enhancement element 202 having a truncated dome shape 208 can be oriented such that the smaller of the two substantially flat surfaces 210 can be pointing outward from the posterior surface of an implant 102.

In operation when installed, an enhancement element 202 can rest between the chest wall and the inward facing (posterior) side of the breast implant 100 and occupies volume within the body and behind the breast implant 100 thus displacing the volume of silicone gel (or other contents of the breast implant 100) 104 such that folding or rippling 106 on the outer surface of the flexible membrane 102 is reduced and/or eliminated.

FIGS. 3*a*-5*e* depict alternate embodiments of a system for reducing or eliminating folding and/or rippling of an implanted breast implant.

In the embodiment depicted in FIGS. 3*a*-3*e* an enhancement element 202 can have a dome shape 203 with an arced surface and a substantially flat rear side 205. As shown in FIG. 3a, a substantially flat rear side 302 can be positioned adjacent to the rear side of an implant 102. In some embodiments, the interface 304 between the arced surface and the substantially flat rear side 302 can be curved and/or smoothed. As shown in FIG. 3e, in some embodiments an enhancement element 202 having a dome shape 203 can be oriented such that a domed surface 203 can be adjacent to the rear of an implant 100.

In the embodiment depicted in FIGS. 4a-4e an enhancement element 206 can have a tubular shape with a substantially flat surface and a substantially flat rear side 302 and a substantially flat top surface. In some embodiments, the interface 402 between the substantially flat top surface and the wall of the tube can be curved and/or smoothed. In further alternate embodiments, the interface 404 between the substantially flat lower surface 302 and the wall of the tube can be curved and/or smoothed. In still further alternate embodiments, the interface 406 between the substantially flat lower surface 302 and the wall of the tube can be other than smoothed.

Figures 4A, 4B, 4C, 4D, 4E, 5A, 5B, 5C, 5D, 5E:
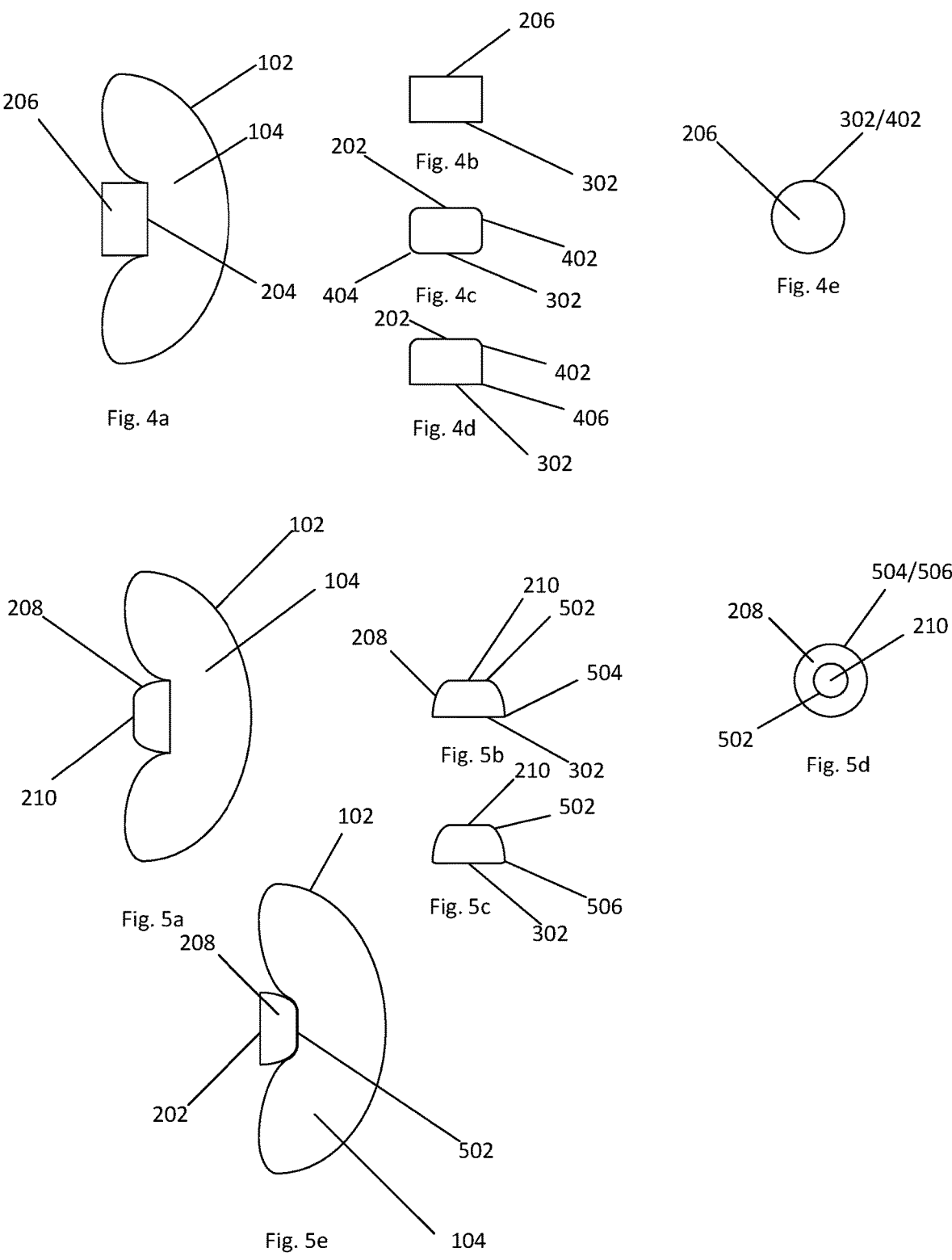

In the embodiment depicted in FIGS. 5a-5e an enhancement element 202 can have a truncated dome shape 208 with an arced surface and a substantially flat rear side 302. In some embodiments, the interface 502 between the substantially flat top surface and the arc of the come can be curved and/or smoothed. In further alternate embodiments, the interface 504 between the substantially flat lower surface 302 and the arc of the dome can be curved and/or smoothed. In still further alternate embodiments, the interface 504 between the substantially flat lower surface 302 and the wall of the tube can be other than smoothed. As shown in FIG. 5e, in some embodiments an enhancement element 202 having a truncated dome shape 208 can be oriented such that the smaller of two substantially flat surfaces 210 can be adjacent to the rear of an implant 100.

Figures 6A, 6B:
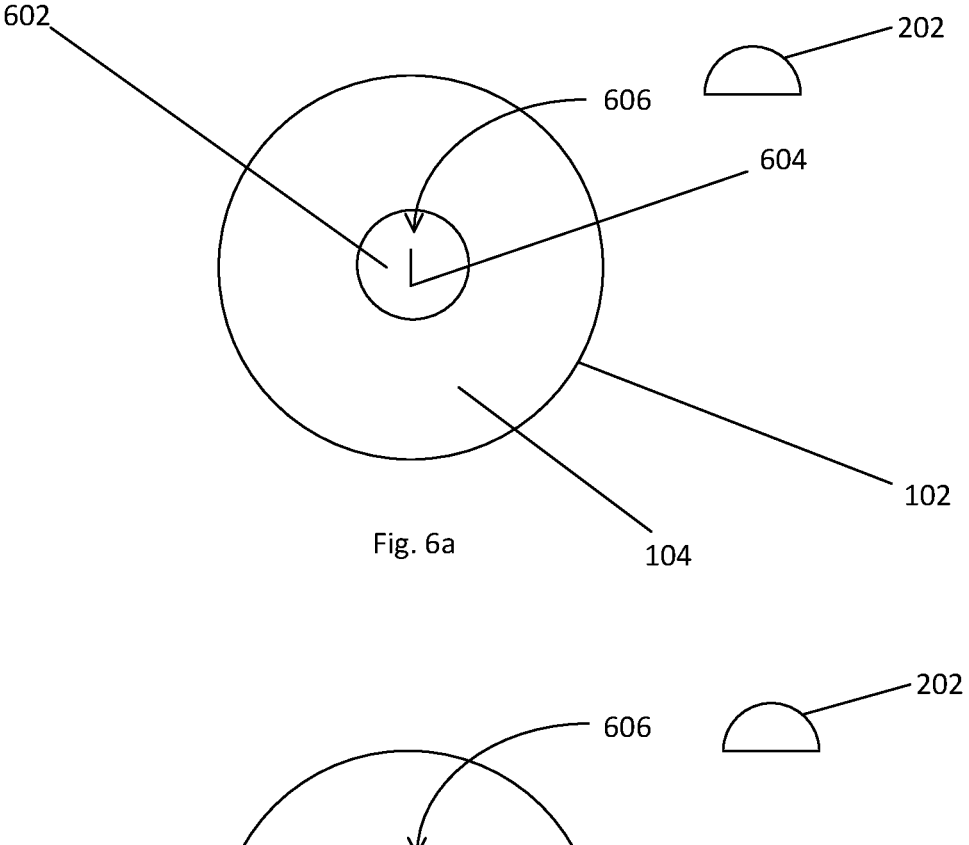
FIGS. 6*a*-6*b* depict alternate embodiments of a device for reducing or eliminating folding and/or rippling of an implanted breast implant.
Figures 7A, 7B, 7C, 7D:
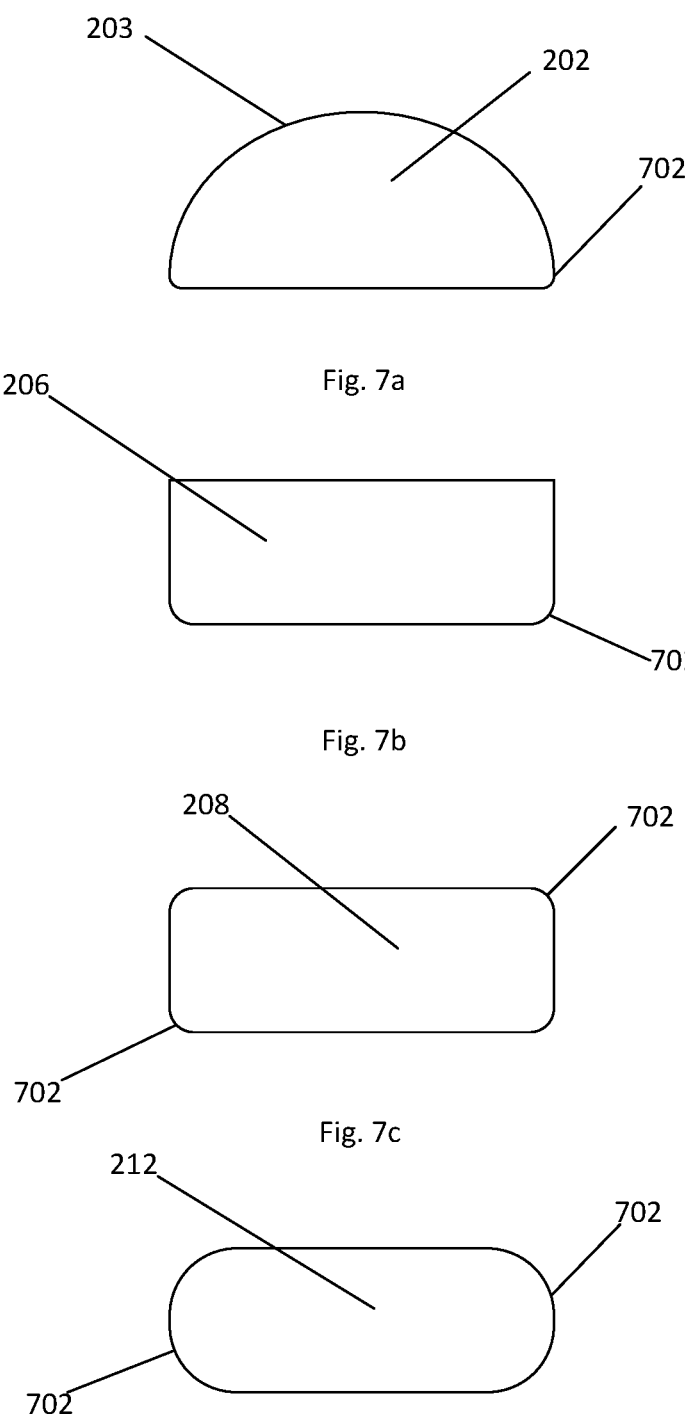
FIGS. 7*a*-7*d* depict alternate embodiments of a device for reducing or eliminating folding and/or rippling of an implanted breast implant.

FIGS. 6a-6b depict alternate embodiments of a system for reducing or eliminating folding and/or rippling of an implanted breast implant. In the embodiment depicted in FIG. 6a, the breast implant 100 can comprise a flexible membrane pocket 602 on the inward facing side of the flexible membrane 102 and the flexible membrane pocket 602 can comprise an aperture 604 to facilitate insertion 606 of an enhancement element 202/206/208 within a flexible membrane pocket 602.

In the embodiment depicted in FIG. 6b, the breast implant 100 can comprise a plurality of flexible retention straps 608 on the inward facing side of the flexible membrane 102 and the flexible retention straps 608 can facilitate coupling 606 of an enhancement element 202/206/208 within the breast implant 100.

As shown in FIGS. 7a-7d, in some embodiments an enhancement element 202/206/208/212 can have at least one angled edge 702, which can be radiused to a degree to reduce sharpness. The edges an enhancement element 202/206/208/212 can be configured to be capable of being in direct contact with the flexible membrane 102 of a breast implant 100 without puncturing, slicing, or otherwise breaking through the flexible membrane 102.

Figure 8:
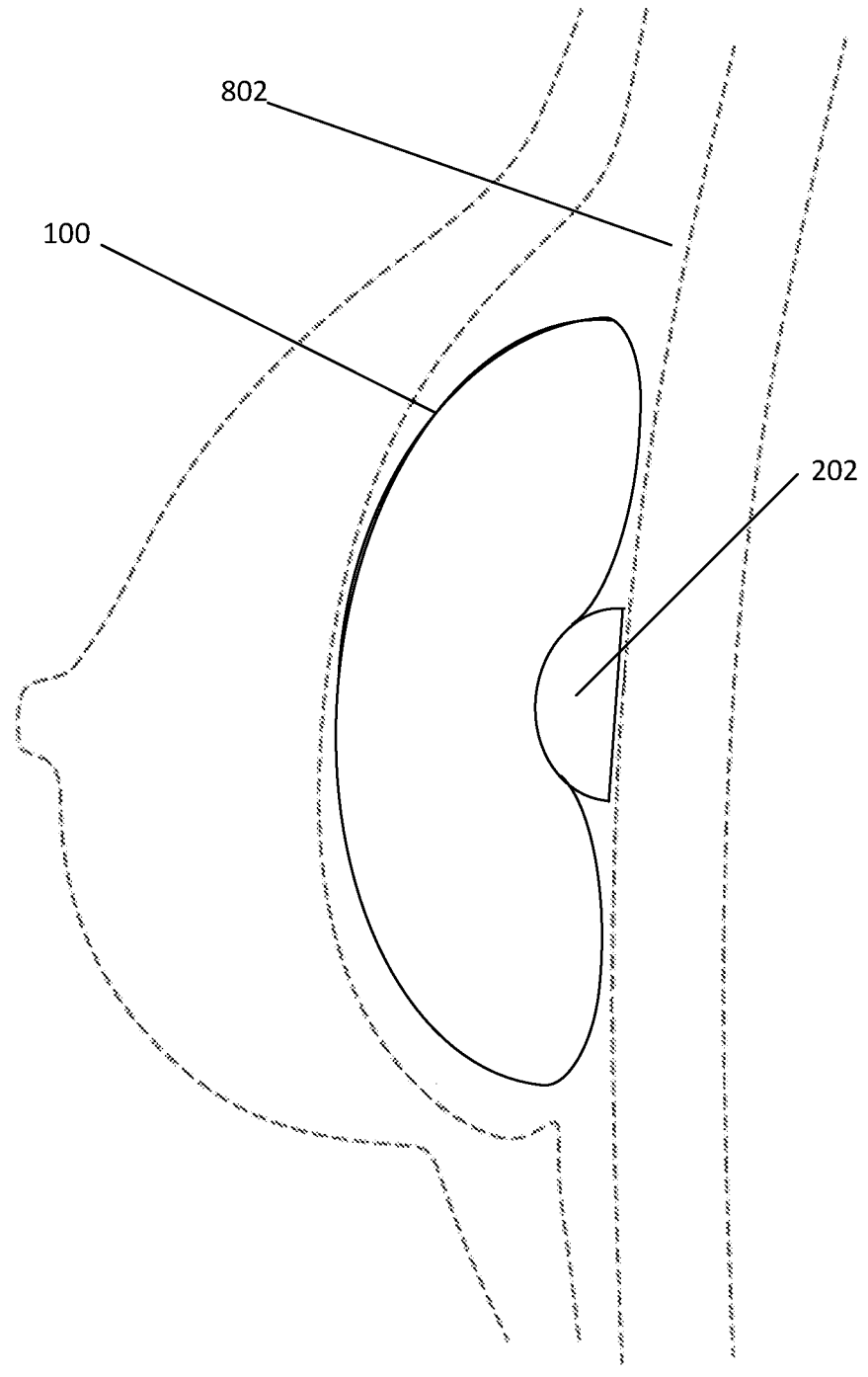
FIG. 8 depicts an embodiment of the current device in use.

In use, as shown in FIG. 8, an enhancement element 202 can be placed anterior to the chest wall 802 and posterior to a breast implant 100. An enhancement element 202 can be affixed to or removably attached to a breast implant 100. In place, an enhancement element 202 can support the contents 104 of a breast implant 100 to prevent wrinkling or folding on the implant 100, which can be visible as wrinkling on the skin.

Figures 9A, 9B, 9C, 9D:
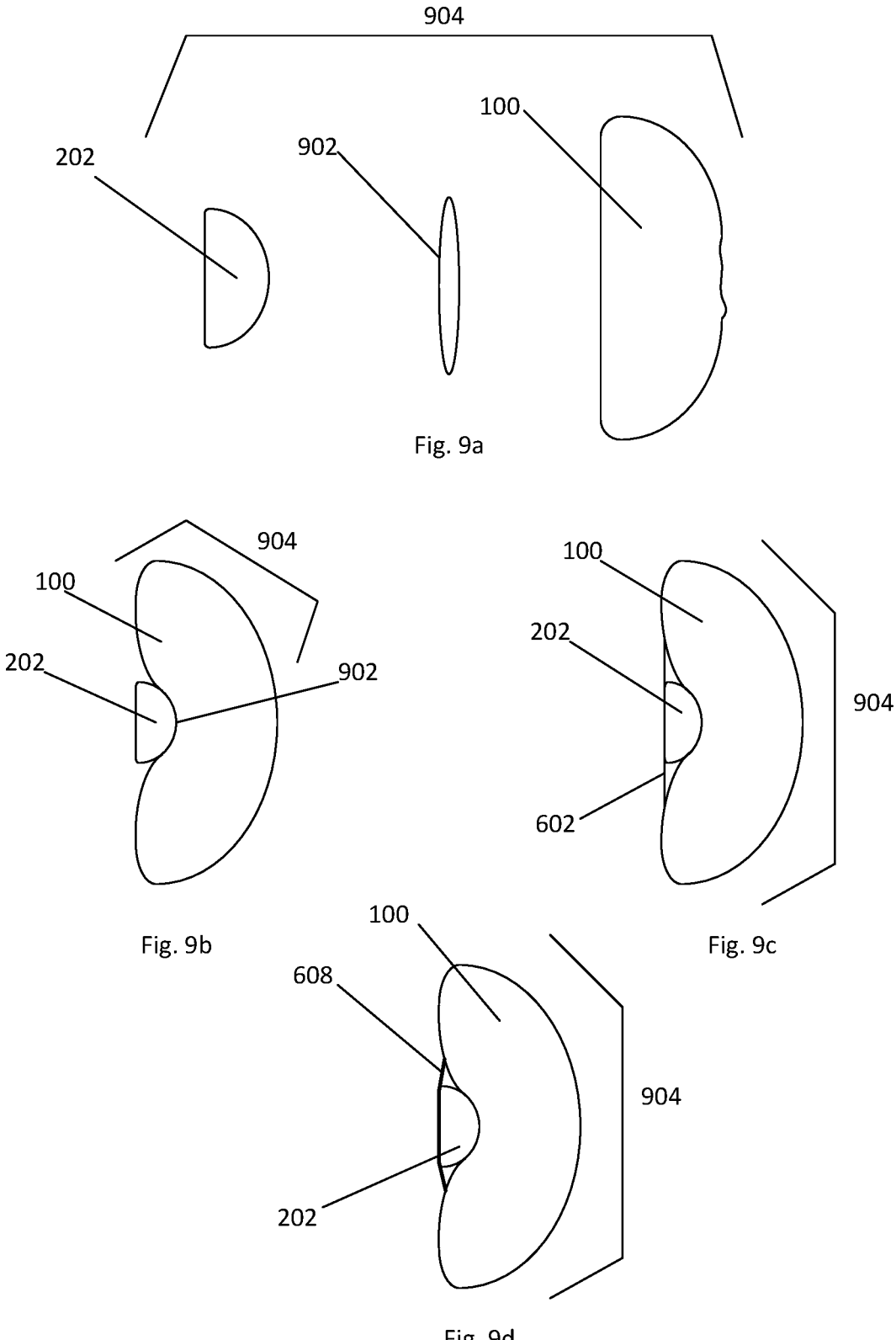
FIGS. 9*a*-9*d* depicts alternate embodiments of systems of the present device.

FIGS. 9a-9d depict further embodiments of systems of the present system. In some embodiments, as shown in FIG. 9a, an enhancement element 202 can be a stand-alone device separate from a breast implant 100. In such embodiments, a user can affix an enhancement element 202 to the posterior surface of an implant 100 either before or at the time of surgery to ensure proper placement. An enhancement element 202 can be affixed to an implant 100 via a polymer weld, a biocompatible adhesive 902, or any other known and/or convenient device.

As shown in FIG. 9b, an enhancement element 202 can be integrated with an implant 100 to create an implant-enhancement system 904. In such embodiments, an enhancement element 202 can be fused to the posterior surface of an implant 100. Different combinations of implants 100 and configurations of enhancement elements 202/206/208/212, as well as enhancement element 202 orientations, can create different types of systems 904.

As shown in FIG. 9c, an enhancement element 202 can be selectively coupled with an implant via a pocket 602. In such embodiments, an enhancement element 202 can be placed into a pocket 602 on the posterior surface of an implant 100 to create an implant-enhancement device system 904. Different combinations of implants 100 and configurations of enhancement elements 202/206/208/212, as well as enhancement element 202 orientations, can create different types of systems 904.

As shown in FIG. 9d, an enhancement element 202 can be selectively coupled with an implant 100 via a plurality of flexible straps 608. In such embodiments, a plurality of flexible straps 608 attached to the posterior surface of an implant 100 can be placed around or over an enhancement element 202 on the posterior surface of an implant 100 to create an implant-enhancement device system 904. Different combinations of implants 100 and configurations of enhancement elements 202/206/208/212, as well as enhancement device 202 orientations, can create different types of systems 904.

Although exemplary embodiments of the invention have been described in detail and in language specific to structural features and/or methodological acts above, it is to be understood that those skilled in the art will readily appreciate that many additional modifications are possible in the exemplary embodiments without materially departing from the novel teachings and advantages of the invention. Moreover, it is to be understood that the subject matter defined in the appended claims is not necessarily limited to the specific features or acts described above. Accordingly, these and all such modifications are intended to be included within the scope of this invention construed in breadth and scope in accordance with the appended claims.

What is claimed:

1. A breast implant enhancement system comprising:
a flexible membrane enclosing contents and having an inner surface, an outer surface and a posterior side; and
an enhancement element positioned outside of said flexible membrane, selectively coupled with said outer surface of said posterior side of said flexible membrane;
wherein said enhancement element has a fixed volume and is sufficiently rigid to displace sufficient breast implant content to prevent folding or rippling on the outer surface of the flexible membrane when in use; and
wherein said enhancement element has at least one angular edge.

2. The breast implant enhancement system of claim 1, further comprising an attachment mechanism adapted and configured to couple the enhancement element with a breast implant.

3. The implant enhancement system of claim 2, wherein said attachment mechanism comprises a friction weld.

4. The implant enhancement system of claim 2, wherein said attachment mechanism comprises a biocompatible adhesive.

5. The breast implant enhancement system of claim 2, further comprising a breast implant.

6. The implant enhancement system of claim 5, wherein said attachment mechanism comprises a pocket affixed to the inward facing side of a breast implant.

7. The implant enhancement system of claim 5, wherein said attachment mechanism comprises at least one flexible retention strap.

8. The implant enhancement system of claim 1, wherein said enhancement element has a domed configuration.

9. The implant enhancement system of claim 1, wherein said enhancement element has a substantially tubular configuration.

10. The implant enhancement system of claim 1, wherein said enhancement element has a truncated substantially domed configuration.

11. The implant enhancement system of claim 1, wherein said at least one edge is radiused.

12. The implant enhancement system of claim 1, wherein said enhancement device further comprises an outer shell of a first material filled with a second material.

13. The breast implant enhancement system of claim 5, wherein said enhancement element and said breast implant are integrated.

\* \* \* \* \*